United States Patent [19]

Lindqvist et al.

[11] Patent Number: 5,375,611
[45] Date of Patent: Dec. 27, 1994

[54] METHOD FOR PREVENTING SECONDARY CATARACT

[75] Inventors: Bengt Lindqvist, Myskdalen; Per Mansson, Sollentuna; Tomas Malson, Uppsala, all of Sweden

[73] Assignee: Pharmacia AB, Uppsala, Sweden

[21] Appl. No.: 8,947

[22] Filed: Jan. 26, 1993

[51] Int. Cl.$^5$ ............................................. A61B 17/00
[52] U.S. Cl. ..................................... 128/898; 604/49
[58] Field of Search ........................... 128/897-898; 604/49, 20, 172; 424/85.8; 435/240.27

[56] References Cited

U.S. PATENT DOCUMENTS

| | | | |
|---|---|---|---|
| 4,432,751 | 2/1984 | Emery et al. | 604/49 |
| 4,966,577 | 10/1990 | Crosson et al. | 604/49 X |
| 5,202,252 | 4/1993 | Emery et al. | 435/240.27 |
| 5,224,957 | 6/1993 | Gasser et al. | 128/898 X |

FOREIGN PATENT DOCUMENTS 0286433 10/1988 European Pat. Off. .
0299467 1/1989 European Pat. Off. .

OTHER PUBLICATIONS

Rose, G. E., "Fibrinous Uveitis and Intraocular Lens Implantation. Surface Modification of Polymethyl-Methacrylate During Extracapsular Cataract Surgery", & Ophthalmology (U.S.) 1992, 99 (8) pp. 1242–1247 (Abstract only).

Olson, R. J., et al.: "Polyvinyl Alcohol as a Protective Coating on Intraocular Lenses", & Arch Ophthalmol (U.S.) Oct. 1980, 98 (10) pp. 1840–1842. (Abstract only).

Matsumoto, T. et al.: "Fibrin Deposits on the Surface Modified PMMA IOLsa", & Nippon Ganka Gakkai Zasshi (Japan) Jan. 1989, 93 (1) pp. 118–123. (Abstract only).

Thierry, David, et al., Biphasic Effect of the Mitotoxin bFGF-Saporin on Bovine Lens Epithelial Cell Growth: Effect of Cell Density and Extracellular Matrix—Journal of Cellular Physiology 153:483–490 (1992).

Primary Examiner—Angela D. Sykes
Attorney, Agent, or Firm—Pollock, Vande Sande & Priddy

[57] ABSTRACT

Method for extracapsular cataract extraction with or without posterior chamber intraocular lens implantation comprising chemical modification of the posterior surface of the lens capsule, at least in the optical portion of said capsule, for preventing cell attachment and growth.

14 Claims, No Drawings

METHOD FOR PREVENTING SECONDARY CATARACT

The present invention is related to the field of ophthalmology and more specifically to methods and means for preventing secondary cataract, a longterm complication after extracapsular cataract extraction with or without intraocular lens implantation.

A great number of intraocular lens (IOL) models have been developed and tested over the years and these as well as the techniques for implantation have been improved so that extracapsular cataract extraction with intraocular lens implantation are now well established procedures with a high success rate. Opacification of the posterior capsule in the optical axis is however still a significant longterm complication, reported to occur in about 50% of the cases after two to five years. This condition is often referred to as secondary cataract or after-cataract.

The risk for opacification seems to be less pronounced with older patients and young age is considered to be the most significant risk factor. It is also to be noticed that even if a surgeon routinely uses a particular implantation technique and the same IOL type, the results might differ in a quite unpredictable way. Very good results with no opacification are obtained in some patients while others, operated under similar conditions, suffer from severe opacification. Prevention of opacification is accordingly of great importance in order to improve the long term outcome of cataract surgery.

A number of techniques for preventing secondary cataract have been tested over the years, both with regard to the IOL as such and the technique used for surgery. One such example is the barrier ridge IOL described by Hoffer (U.S. Pat. No. 4,244,060). One aim of this design was to create a mechanical barrier to inhibit migration of residual lens epithelial cells and their derivatives into the optical zone behind the IOL.

Secondary cataract is treated by making an opening in the opcified posterior len capsule. This opening is today usually made with a NdYag laser. A laser beam is shot through the pupil and the IOL and focused on the posterior lens capsule. Several complications have been observed with this method which is reported to increase the incidence of retinal detachment and cystoid macular oedema.

The object of the present invention is to provide an improved method for preventing opacification in connection with extracapsular cataract extraction and intraocular lens implantation, by chemical modification of the posterior capsule wall in order to decrease adhesion and proliferation of cells.

Surface modification of devices for implantation in general, in order to provide a surface with desired cell interaction characteristics, has been utilised for a long time. In certain applications the aim is to completely avoid cell attachment, while good cell attachment and growth is essential for good results in other applications. Hydrophilic as well as hydrophobic surfaces have been developed for this reason and there are also examples when the surface has been modified chemically with positive charges and various other functional groups in order to increase cell adhesion. Various heparin coatings, frequently used when preparing catheters of various kinds for insertion, are examples of hydrophilic surface modifications having very specific biological activity. Other examples of compounds also giving very hydrophilic surfaces are polyethylene glycol (PEG), dextran and phosphatidyl choline. The unique properties regarding protein/cell rejection of a PEG coated surface have been explained by an extensive hydration of the surface layer in the aqueous phase, which gives rise to a steric repulsion force between the very mobile PEG-molecules and components outside the surface such as proteins and cells. Hydrophobic surfaces utilized in certain connections have been obtained by applying a layer of for instance silicone or a tetrafluoroethylene polymer (Teflon). There are only a few publications, as far as we know, which are related to surface modifications of living tissue. In one such example (Pathak C. P., Sawhney A. S., Dunn R. C. and Hubbel J. A. Fourth World Biomaterial Congress Berlin 1992 Transactions and final program p. 231) rat cecum and rabbit uterine horn were modified with a biodegradable hydrogel (polyethylene glycol glycolidyl diacrylate). The surfaces of the tissues were reported not to be biologically adhesive and formed a biocompatible mechanical barrier to prevent adhesions.

Modification of the lens capsule according to the present invention is characterized by chemical modification of the capsule, resulting in a stable deposit which for instance can be covalently linked to chemical groups in the tissue or forming an interpenetrating network with the lens capsule tissue. Polymers can also have particular structures with adhesive properties like the 2,3-dihydroxyphenylalanine rich polyphenolic protein secreted by the marine mussel Mytilus Eulis (Waite J. H., Chem. Tech. Nov. 1987 p. 692–697) and polymers containing the RGD peptide sequence (Piersbacher, M. D and Ruoslahti, E., Nature 1984, 309, 30–33) would also show affinity for tissue.

The stable or permanent layer that is created in accordance with this invention is water-insoluble and is clearly distinguished from the temporary layer that is created when for example hyaluronic acid is injected into the capsule in connection with implantation of an intraocular lens.

In one embodiment of the invention polymers, for example polyethylene glycol (PEG), polysaccharides, polyethylenepolypropylene glycol (poloxamer, i.e. Pluronic and Synperonic), and polyvinyl alcohols are derivatized to contain active groups which are used for grafting crosslinking or polymerizing the macromonomer onto the tissue.

Derivatives useful in this connection include those reacting with carboxylic groups, hydroxyl groups, amino groups or thiol groups of proteins in the lens capsule tissue. As examples of such derivatives can be mentioned aldehydes, anhydrides, activated esters such as: (alkyl-oxy-formyl) carboxylates, nitrophenyl carbonate esters, carboxylate succinimidyl esters, carbonate succinimidyl ester, carboxylate p-nitrophenyl ester, oxycarbonylimidazole, trifluoro acetates; alkyl and arylsulfonates such as toluene sulfonates; methyl sulfonates, trifluoroethyl sulfonates; carboxymethyl hydrazides that upon treatment with nitrite forms the corresponding carboxymethyl azide; thiols, epoxides, isocyanates, 5-phenylisoxazolium-3'-sulfonate derivatives; halogenides like chloride, bromide and iodide; cyanuric chloride derivatives; and aryl azides, that form covalent linkages to the lens capsule upon UV irradiation.

In a preferred aspect of the invention the derivatised polymer is PEG.

Examples of polysaccharides and derivatives thereof are mucopolysaccharides like hyaluronic acid, heparin, chondroitin sulfates and dermatan sulfate; dextran, starch and starch derivatives like carboxymethyl starch, cellulose and cellulose derivatives like carboxymethyl cellulose and hydroxypropylmethyl cellulose.

Interpenetrating networks are formed when monomeric or macromeric substances are first allowed to diffuse into tissue and then polymerized. This can be achieved by monomers or macromers containing polymerizable groups or derivatized to contain such groups. Examples of compounds and substituents suited for radical polymerization are acrylic amides and esters, cinnamic derivatives, vinyl esters and styrene derivatives.

Examples of macromer backbones are PEG and polyethylene glycol polypropylene glycol copolymers (poloxamers like Pluronic and Synperonic).

Radical polymerization can be accomplished thermally with initiators of for instance peroxide or azo compounds like banzoylperoxide, azoisobutyronitrile and ammonium persulfate, or by irradiation.

In order to increase the rate of initiation in the peroxide system at body temperatue (around 37° C.) a promotor is preferrably added. Examples of such promotors are metals like Co, Fe, Mn, V, Cu etc., and tertiary amines like N,N,N',N'-tetramethyl-ethylenediamine (TEMED). The peroxide and the promotor form a redox system, which creates the radicals necessary for polymerization and/or crosslinking of the monomers or macromonomers used. The at present preferred systems are prepared by using hydrogen peroxide and ammonium persulfate resp. TEMED and Fe.

Another way of starting the reactions of the double bond functionalized macromonomers is to initiate the reaction by irradiation. In this process the macromonomers are subjected to an excitation energy, which is sufficient to produce radicals directly on the macromonomer or on a photo-initiator, which will start the reactions. The active radicals can then be used as a grafting site for grafting onto the tissue on the capsule or start propagation (polymerization) of the double bonds forming an interpenetrating network.

Yet another way of depositing polymers and probably to some extent obtain covalent substitution with subsequent formation of an interpenetrating network with the lens capsule tissue is the use of condensation polymerization as illustrated in Example 10 below where PEG carboxylic acid chloride and polyoxypropylene amine is reacted with each other.

In a further embodiment of the invention a polyvinyl alcohol titanium complex was deposited on the lens capsule tissue, resulting in substantial reduction of the growth of lens epithelial cells.

Complex formation to obtain water insoluble coatings can naturally be obtained in several ways for example based on charge interactions between two oppositely charged polyelectrolytes.

Binding various molecules to a surface is known from several technical fields and already the techniques used in one such area, chromatography, indicate a large number of ways to obtain a desired deposit as soon as the general concept is known from this specification.

One specific example can be mentioned in this connection: nitrite activation of heparin as disclosed in U.S. Pat. No. 4,810,784 (Larm), for binding heparin in a controlled way to an amino group rich substrate.

We have also found that besides using compounds of the type mentioned above, also low molecular weight compounds can be utilized in the modification of lens capsule tissue. Treatment of lens capsule with bromoacetic acid introduces carboxylic groups, creating a negatively charged surface at physiological pH. Also such a layer of low molecular weight substituents forming a charged surface are within the scope of the term deposit as used in this connection. Treatment of the lens capsule with reagents for creating the deposit can be done in that monomers, macromers, polymers or any other component needed for the reaction are dissolved in a biologically acceptable solvent like dimethylsulfoxide and placed on the tissue whereafter the reaction is initiated and the desired layer is formed. Any remaining and unreacted components are then removed by washing the tissue with a physiologically acceptable aqueous solution, preferably containing also hyaluronic acid which is frequently used in various ophthalmological applications. Water insoluble polymers can also be deposited on lens capsule tissue if applicated as a solution in a biologically acceptable solvent. When water is added the polymer is precipitated on the tissue.

The invention will now be illustrated by a series of examples which for obvious reasons are carried out in an in vitro test system. This system has been designed to be relevant to the in vivo situation so that lens epithelial cells attachment and morphological development can be evaluated on a modified model substrate.

As model substrates posterior lens capsules or extra capsular matrix (ECM) coated culture dishes (Biological Industries Kibbutz Beth Haemek Israel) have been used.

The lens epithelical cells used were cultured in the following way: New Zealand White rabbit lenses were removed from freshly enucleated eyes, the anterior capsules were isolated and cut in pieces. The capsular pieces with adherent LEC were cultured in Dulbeccos Modified Eagle Medium supplemented with 10% fetal calf serum 20% Hams' F-12, 1% Non Essential Amino Acids, 1% L-Glutamine and 1% Antibiotic Antimycotic Solution (all from Gibco). After reaching confluence, the cells were passed with 0.05% trypsin and 0.02% EDTA for 10 minutes and split 1:3. The cells were incubated at 37° C. and 5% $CO_2$.

The lens capsules were prepared according to the following procedure using fresh bovine cadaver eyes: An equatorial cut was made through the eye globe with a pair of scissors and the vitreous was removed. The remaining vitreous on the posterior part of the lens capsule was removed with a cotton swab. The lens capsule was cut into an anterior and a posterior part with a pair of scissors. The posterior part was transferred to a glass plate with the interior surface upwards, was then allowed to dry and was finally fixed onto the glass plate with a ring of silicone rubber (RTV Silicone GEC) that also forms a well for fluid treatment of the capsule surface.

Before and after the various treatment procedures the lens capsules were thoroughly rinsed with physiological saline solution. The capsules were stored in such a solution until they were used for cell adhesion experiments.

Cell incubation on the surfaces used for the tests was standardised as follows: In the 4th passage the cells were transferred to the lens capsules and culture dishes for the attachment experiments. 10,000–20,000 cells were used per capsule and approximately 50,000 cells per culture dish. The samples were incubated for 48 hours as described above. The culture medium was removed and the cells were fixed in 1% glutaraldehyde, rinsed with PBS and stained with Mayer's Hematoxylin for 15 minutes. The samples were rinsed in tap water and the cellular adhesion and morphology was evaluated using a light microscope.

The surfaces of the unmodified capsules and culture dishes were completely covered with lens epithelial cells after the incubation procedure. The morphology of the cells was either the typical epithelial polygonal one or a more irregular morphology with flattened and more spread out cells. The cells appeared viable with a proliferative capacity.

In all the examples given below the modification procedures described have given rise to surfaces exhibiting significant reduction of the lens cell attachment to the modified substrate surface. The morphology of the cells showed that the cells were rounded and unable to spread out and consequently not able to completely attach. After 48 hours in culture the cells showed no proliferative capacity. It should be noticed that for in vivo use some of these methods might require special administration procedures.

EXAMPLE 1

Lens Capsule Modification with (isobutyl-oxy-formyl) PEG Succinate

Monomethoxy PEG3000 (MeOPEG3000-Hoechst) was converted to the succinate ester through reaction with succinic anhydride in pyridine according to Abuchowski et al (Cancer Biochem Biophys 7 (1984) 176).

5 g MeOPEG3000 succinate ester was dissolved in 40 ml methylene chloride. 490 μl triethylamine and 481 μl isobutyl chloroformate were added. The solution was stirred for 30 minutes after which the solvent was evaporated at 30° C. The residue was washed five times with 50 ml petroleum ether portions.

The substance was used for treatment of lens capsules and ECM coated culture dishes. 175 mg of the substance was quickly moistened in 1 ml 0.25M borate buffer pH 8 or 9.5. Before the substance had dissolved it was applied onto the lens capsule or the culture dish. The surfaces were treated for 5 minutes each. The PEG substitution was also confirmed by ESCA spectroscopy.

EXAMPLE 2

Lens Capsule Modification with a 5-phenylisoxazolium-3'-sulfonate Derivative of PEG 3 g of methoxy PEG3000 succinate ester was dissolved in 25 ml dry acetonitrile. The solution was cooled in an ice bath. 139 μl triethylamine was added and thereafter 0.253 mg N-ethyl-5-phenylisoxazolium-3'sulfonate. The solution was stirred for 2 hours while the solution was allowed to obtain room temperature. The solvent was evaporated and the substance washed twice with petroleum ether.

250 mg of this derivative was rapidly dissolved in 0.25M borate buffer pH 9.5. The solution was immediately applied onto a lens capsule for 5 minutes. The coating procedure was repeated one more time.

EXAMPLE 3

Lens Capsule Modification with Azido Derivatives of PEG 300 mg PEG1000 (Fluka) was dissolved in toluene and the solvent was evaporated, This procedure was repeated one more time, The substance was dissolved in 5 ml 60% potassium hydroxide solution, 80 mg 4-azido-1-fluoro-2-nitrobenzene (Aldrich) dissoved in 10 ml toluene was mixed with the PEG solution, The two phase system was stirred rapidly in the dark for three days, Thin layer chromatography of the toluene phase revealed a mixture of di-and monosubstituted PEG-azido derivatives, The toluene phase was shaken with water, The monoazido substituted derivative was partitioned into the water phase and the diazido derivative was retained in the toluene phase, The phases were evaporated to dryness, 40 mg of the dry monoazido substituted material was dissolved in 0.5 ml water, The solution was applied onto a lens capsule that was UV irradiated for 10 minutes, The diazido derivative obtained from evaporation of the toluene phase was also used, 20 mg of this material was emulsified in water in an ultrasonic bath, The emulsion was applied onto lens capsules that were irradiated with UV light (UV lamp Philips TL K40W/09N 90mW/cm$^2$) for 15 minutes,

EXAMPLE 4

Lens Capsule Modification with an Azido Derivative of Polyvinyl Alcohol (PVA)

300 mg PVA (100% hydrolysed M$_w$ 14,000 EGA Sweden) was dissolved in 5 ml water during heating, 1 g potassium hydroxide was added, The solution was cooled to room temperature, 75 mg 4-azido-1-fluoro-2-nitrobenzene was dissolved in 10 ml toluene and mixed with the PVA solution, The two phase system was vigorously stirred in the dark over night, 25 ml water was added to the formed emulsion and the mixture was centrifuged, The water phase was separated and neutralised with acetic acid and dialysed against distilled water to a final volume of approximately 35 ml.

The dialysed PVA solution was applied onto a lens capsule for 5 minutes. The solution was withdrawn and the capsule was UV irradiated (as in example 4) for 10 minutes.

EXAMPLE 5

Lens Capsule Modification with Epoxy Activated Dextran 2 g dextran Mw 20,000 (Dextran T20 Pharmacia Fine Chemicals) was dissolved in 20 ml 0.5% NaOH solution. 2 g 1,4-butanediol diglycidyl ether was added to the solution which was stirred for half an hour and dialysed overnight. The product was precipitated in ethanol and dried.

100 mg of the thus obtained epoxy activated dextran was dissolved in 1 ml borate buffer pH 9.5. The solution was applied onto a lens capsule for half an hour.

EXAMPLE 6

Lens Capsule Modification with Bromoacetic Acid 50 mg bromoacetic acid was dissolved in 5 ml borate buffer pH 9.5. A lens capsule was treated with the solution for 3 hours.

EXAMPLE 7

Lens Capsule Modification with Polyacrylonitrile 25 mg polyacrylonitrile M$_w$ 150,000 (Polysciences) was dissolved in 1 ml dimethyl sulfoxide (DMSO). The solution was applied to a lens capsule for 5 minutes. The capsule was then briefly washed with DMSO and subsequently with saline.

EXAMPLES 8 a and b

Lens Capsule Modification with PEG-acrylates a) 0.3 g PEG-diacrylate 400 (Polysciences) and 5 mg N,N,N',N'-tetramethylenediamine (TEMED) was dissolved in 1 ml of saline. Nitrogen was bubbled through the solution for 4 minutes in order to remove oxygen. The solution was then applied onto a lens capsule for 5 min whereafter the solution was withdrawn and replaced with a solution of ammonium persulfate (0.5% in 0.9% saline) for 5 minutes. This persulfate treatment was repeated once.

b) 0.4 g PEG-diacrylate 400 and 10 mg $FeSO_4$ was dissolved in 1 ml of saline. Nitrogen gas was bubbled through the solution for 4 minutes in order to remove oxygen. The solution was then applied onto a lens capsule for 5 min, whereafter the solution was withdrawn and replaced with a solution of hydrogen peroxide (2% in 0.9% saline) for 5 minutes.

c) 0.3 g PEG-diacrylate 400 and 5 mg of the initiator Quantacure BTC (Ward Blenkinsop.) were dissolved in 1 ml saline solution. The solution was applied onto a lens capsule for 5 min, whereafter the solution was withdrawn and the capsule was subjected to UV irradiation (as in example 3) for 2 minutes.

EXAMPLE 9

Lens Capsule Modification with Acrylated Poloxamer 25 g poloxamer (propylene-ethylene oxide copolymer—Synperonic F127 Mw 12,000 ICI) was treated with toluene as in Example 3. The substance was dissolved in 175 ml methylene chloride. The solution was cooled in an ice bath and 6.67 ml pyridine and 7.23 ml acryloyl chloride were added. The solution was stirred and allowed to reach room temperature overnight.

200 ml methylene chloride was added and the solution was filtered. The filtrate was precipitated in 2,500 ml diethyl ether. The precipitated substance was dissoved in water and dialysed overnight. The dialysed solution was lyophilised.

125 mg of the dried substance was dissolved in 1 ml 0.9% saline. 6.4 μl TEMED was added and the solution degassed with nitrogen. The solution was applied onto a lens capsule for 5 minutes whereafter the solution was withdrawn and replaced with a solution of ammonium persulfate (0.5% in 0.9% saline) for 5 minutes. The persulfate treatment was repeated once.

EXAMPLE 10

Lens Capsule Modification with a Condensation Polymer of PEG Dicarboxylic Acid Chloride and Polyoxypropyleneamin 10 g PEG600-diacid (Fluka) was treated with toluene as in Example 3. The substance was dissolved in 75 ml methylene chloride. The solution was cooled to 0° C. under nitrogen. 5 ml thionyl chloride was added and the solution stirred overnight. The solvent was evaporated, 50 ml toluene added and the solvent was then evaporated once again.

2 g polyoxypropylene triamine (Jeffamine T-403, Texaco) was dissolved in 20 ml water. The pH of the solution was lowered to 9.5 with hydrochloric acid. The solution was applied onto a lens capsule for 5 minutes and thereafter withdrawn. 0.2 g of the PEG acid chloride was quickly dissolved in 2 ml water and instantly applied to the pretreated lens capsule and left for one minute.

EXAMPLE 11

Lens Capsule Modification with a PVA Titanium Complex 500 mg PVA (see Example 4) was dissolved in 10 ml 0.9% saline with heating. The solution, cooled to room temperature, was applied to a lens capsule for 15 minutes. The lens capsule was then rinsed with saline.

300 mg TYZOR$^R$TE (titanium isopropoxy(triethanolaminato)-isopropyl alcohol from du Pont) was dissolved in 2 ml water. The pretreated lens capsule was treated with this solution for 1 minute.

We claim:

1. Method for extracapsular cataract extraction with or without posterior chamber intraocular lens implantation characterized in that the posterior surface of the lens capsule, at least in the optical portion of said capsule, is chemically modified for preventing cell attachment and growth, wherein a water-insoluble stable layer of a cell attachment preventing compound is deposited onto the posterior surface of the lens capsule.

2. The method of claim 1 wherein the layer is covalently bound to the capsule tissue.

3. The method of claim 1 wherein the layer forms an interpenetrating network with the capsule tissue.

4. The method of claim 3 wherein said network is formed by diffusing a monomeric or macromeric substance into capsule tissue and then polymerizing said substrate.

5. The method of claim 4 wherein said substance is selected from the group of acrylic amide, acrylic ester, cinnamic derivative; vinyl ester and styrene derivative.

6. The method of claim 1 wherein the layer is a polymer selected from the group consisting of polyethylene glycol, polysaccharides, polyethylenepolypropylene glycol and polyvinyl alcohols.

7. The method of claim 5 wherein said polymer is a derivative containing reactive groups capable of reacting with a group selected from the class consisting of carboxylic group, hydroxyl group, amino group and thiol group.

8. The method of claim 5 wherein said polymer is selected from the group consisting of (isobutyl-oxy-formyl) polyethylene glycol; 5-phenylisoxaozolium-3'-sulfonate derivative of polyethylene glycol; azido derivative of polyethylene glycol; polyethylene glycol diacrylate; condensation polymer of polyethylene glycol dicarboxylic acid chloride and polyoxypropyleneamine; azido derivative of polyvinyl alcohol; polyvinyl alcohol titanium complex; epoxy activated dextran; and acrylated copolymer of propylene oxide and ethylene oxide.

9. The method of claim 5 wherein said polymer is a polyethylene glycol derivative.

10. The method of claim 5 wherein said polymer is a polyvinyl alcohol derivative.

11. The method of claim 1 wherein the layer is a complex.

12. Method for extracapsular cataract extraction with or without posterior chamber intraocular lens implantation characterized in that the posterior surface of the lens capsule, at least in the optical portion of said capsule, is chemically modified by treating with bromoacetic acid or polyacrylonitrile for preventing cell attachment and growth.

13. The method of claim 12 which comprises chemically modifying said optical portion by treating with bromoacetic acid.

14. The method of claim 12 which comprises chemically modifying said optical portion by treating with polyacrylonitrile.

* * * * *